(12) United States Patent
Carlson

(10) Patent No.: US 11,253,704 B2
(45) Date of Patent: Feb. 22, 2022

(54) DEVICES AND METHODS FOR TREATING TINNITUS USING ELECTRICAL STIMULATION

(71) Applicant: Mayo Foundation for Medical Education and Research, Rochester, MN (US)

(72) Inventor: Matthew L. Carlson, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 24 days.

(21) Appl. No.: 16/307,700

(22) PCT Filed: Jun. 2, 2017

(86) PCT No.: PCT/US2017/035617
§ 371 (c)(1),
(2) Date: Dec. 6, 2018

(87) PCT Pub. No.: WO2017/213978
PCT Pub. Date: Dec. 14, 2017

(65) Prior Publication Data
US 2019/0167985 A1    Jun. 6, 2019

Related U.S. Application Data

(60) Provisional application No. 62/346,306, filed on Jun. 6, 2016.

(51) Int. Cl.
*A61N 1/36* (2006.01)
*A61N 1/05* (2006.01)
(Continued)

(52) U.S. Cl.
CPC .......... *A61N 1/361* (2013.01); *A61N 1/0541* (2013.01); *A61N 1/36038* (2017.08);
(Continued)

(58) Field of Classification Search
CPC ................ A61N 1/361; A61N 1/37518; A61N 1/36038; A61N 1/0541; H04R 25/75; H04R 2225/67
See application file for complete search history.

(56) References Cited

U.S. PATENT DOCUMENTS 4,419,995 A * 12/1983 Hochmair ............... A61F 11/04
607/57
4,462,401 A * 7/1984 Burgio ................. A61N 1/0541
128/DIG. 26
(Continued)

FOREIGN PATENT DOCUMENTS

WO     WO 89/06988      8/1989
WO     WO 2010/028152   3/2010
(Continued)

OTHER PUBLICATIONS

Extended European Search Report in European Application No. 17810752.0 dated Nov. 19, 2019, 8 pages.
(Continued)

*Primary Examiner* — Mallika D Fairchild
(74) *Attorney, Agent, or Firm* — Fish & Richardson P.C.

(57) ABSTRACT

Electrical stimulation devices can be used to treat tinnitus. For example, tinnitus can be treated using implantable electrodes and stimulation devices for delivering electrical stimulation to a patient's cochlear region. Cochlear surface electrode(s), endosteal electrode(s), subendosteal electrode(s), intraosseous electrode(s), or short intracochlear electrode(s) (or a combination thereof), connected to existing or modified cochlear implant receiver/stimulator tech-
(Continued)

nology, can provide a successful model for long-term treatment of tinnitus in a large number of patients. In some cases, patients can simply turn on the tinnitus implant when experiencing troublesome tinnitus and gain instant relief.

15 Claims, 4 Drawing Sheets

(51) Int. Cl.
*A61N 1/375* (2006.01)
*H04R 25/00* (2006.01)
(52) U.S. Cl.
CPC ......... *A61N 1/37518* (2017.08); *H04R 25/75* (2013.01); *H04R 2225/67* (2013.01)

(56) References Cited

U.S. PATENT DOCUMENTS

| | | | | |
|---|---|---|---|---|
| 4,809,712 | A * | 3/1989 | Kuzma | A61N 1/0541 607/116 |
| 6,374,143 | B1 * | 4/2002 | Berrang | A61N 1/0541 600/379 |
| 8,285,384 | B2 | 10/2012 | Ball et al. | |
| 8,594,799 | B2 | 11/2013 | Haller et al. | |
| 8,630,721 | B2 | 1/2014 | Gantz | |
| 8,880,193 | B1 | 11/2014 | Thenuwara et al. | |
| 9,089,692 | B2 | 7/2015 | Risi et al. | |
| 9,320,891 | B2 | 4/2016 | Anderson et al. | |
| 2003/0009095 | A1 * | 1/2003 | Skarda | A61B 18/1492 600/374 |
| 2007/0021804 | A1 * | 1/2007 | Maltan | A61N 1/361 607/55 |
| 2007/0203536 | A1 * | 8/2007 | Hochmair | H04R 25/75 607/57 |
| 2010/0121390 | A1 * | 5/2010 | Kleinman | A61B 17/1604 606/86 R |
| 2010/0145162 | A1 * | 6/2010 | Devauchelle | A61N 1/375 600/300 |
| 2010/0305676 | A1 | 12/2010 | Dadd et al. | |
| 2012/0071890 | A1 * | 3/2012 | Taylor | A61B 5/6844 606/129 |
| 2012/0245585 | A1 * | 9/2012 | Kaiser | A61B 17/1633 606/80 |
| 2013/0281812 | A1 | 10/2013 | Pau et al. | |
| 2014/0163692 | A1 | 6/2014 | Van den Heuvel et al. | |
| 2014/0222002 | A1 * | 8/2014 | Maxson | A61B 17/1697 606/80 |
| 2015/0039057 | A1 * | 2/2015 | Della Santina | A61N 1/36032 607/62 |
| 2016/0106498 | A1 * | 4/2016 | Highsmith | A61B 18/1492 606/41 |
| 2016/0324552 | A1 * | 11/2016 | Baker | A61B 17/8033 |
| 2017/0050027 | A1 | 2/2017 | Anderson et al. | |
| 2019/0070413 | A1 * | 3/2019 | Phillips | A61N 1/37211 |
| 2020/0338343 | A1 | 10/2020 | Carlson | |

FOREIGN PATENT DOCUMENTS

| | | |
|---|---|---|
| WO | WO 2010/120979 | 10/2010 |
| WO | WO 2017/213978 | 12/2017 |
| WO | WO 2015/085135 | 6/2019 |
| WO | WO 2020/247125 | 12/2020 |

OTHER PUBLICATIONS

Arts et al., "Optimizing Intracochlear Electrical Stimulation to Suppress Tinnitus," Ear & Hearing, 36(1):125-135, Jan. 2015.
Engineer et al., "Willingness to Accept and Pay for Implantable Tinnitus Treatments: A Survey," Neuromodulation: Technology at the Neural Interface, 16(2):154-162, Mar. 2013.
Pau et al., "Would an endosteal CI-electrode make sense? Comparison of the auditory nerve excitability from different stimulation sites using ESRT measurements and mathematical models," Eur. Arch. Otorhinolaryngol., 271(6):1375-81, Jun. 2014.
PCT International Search Report in International Application No. PCT/US2017/035617 dated Aug. 15, 2017, 2 pages.
PCT Written Opinion in International Application No. PCT/US2017/035617 dated Aug. 15, 2017, 7 pages.
Perez et al., "Multiple Electrostimulation Treatments to the Promontory for Tinnitus," Otology & Neurotology, 36:366-372, Feb. 2015.
Macías et al., "One-year results for patients with unilateral hearing loss and accompanying severe tinnitus and hyperacusis treated with a cochlear implant," Audiology and Neurotology, 23(1):8-19, 2018.

* cited by examiner

DEVICES AND METHODS FOR TREATING TINNITUS USING ELECTRICAL STIMULATION

This application is a National Stage application under 35 U.S.C. § 371 of International Application No. PCT/US2017/035617, having an International Filing Date of Jun. 2, 2017, which claims the benefit of U.S. Provisional Ser. No. 62/346,306 filed Jun. 6, 2016. The disclosures of the prior applications are considered part of (and are incorporated by reference in) the disclosure of this application.

BACKGROUND

1. Technical Field

This document relates to devices for treating tinnitus and methods of treating tinnitus using the devices. For example, this document relates to implantable electrodes and stimulation devices for delivering electrical stimulation to the otic capsule, cochlear region, vestibular region (e.g., vestibule or semicircular canals), the vestibulocochlear nerve, or the brainstem to treat tinnitus. In some cases, an electrode for delivering electrical stimulation is placed endosteally and/or intraosseously, within the bone of the cochlea, including the promontory.

2. Background Information

Subjective tonal tinnitus (i.e., ringing in the ear) is the phantom perception of sound when no external generating stimulus is present. Tinnitus may be unilateral, bilateral or non-localizing, and may present intermittently or continuously.

Subjective tonal tinnitus affects approximately a fourth of the US population and is a major source of disability affecting many domains of life. For some, tinnitus is merely a fleeting annoyance; however for many individuals, tinnitus may cause audiological, neurological or cognitive impairment resulting in poor attention, increased distractibility, anxiety, depression, and even suicide. Tinnitus remains the number one disability experienced by U.S. veterans. In 2011 alone, more than 10 percent of all veteran disability claims were due to tinnitus, making it a top research priority of the U.S. Department of Defense and the Veterans Health Administration.

Despite substantial clinical research in humans and study of animal models, the exact mechanism(s) behind tinnitus remain largely unknown. It is currently held that tinnitus likely reflects inadequate reorganization within the central nervous system following a peripheral auditory system injury. The theory of cochlear deafferentation as a cause for tinnitus parallels phantom limb pain, where cortical maladaptation develops in response to loss of sensory input.

Currently, there are no FDA approved pharmacological therapies or surgical devices available for the treatment of tinnitus. Current treatment methods largely focus on counseling, cognitive behavioral therapy, masking, and sound therapy. Such strategies may help render tinnitus more tolerable, but such strategies do not abolish the symptom or reverse the underlying pathophysiological process.

SUMMARY

This document provides devices for treating tinnitus and methods of using the devices to treat tinnitus. For example, this document provides implantable electrodes and stimulation devices for delivering electrical stimulation to the cochlea region, such as on the surface of the cochlear bone including the promontory, or endosteally and/or intraosseously within the cochlear bone, to treat tinnitus.

In one implementation, an electrode device for delivering electrical pulse stimuli to a patient's cochlear region includes: a lead comprising a single elongate insulated electrical conductor; a single electrode disposed at a distal end of the lead and in electrical communication with the insulated electrical conductor; and an anchor element disposed adjacent to the electrode.

In another implementation, an electrode device for delivering electrical pulse stimuli to patient's cochlear region includes: a lead comprising two elongate insulated electrical conductors; a pair of electrodes disposed at a distal end of the lead, individual electrodes of the pair of electrodes in electrical communication with a single respective electrical conductor of the two electrical conductors; and an anchor element disposed adjacent to the pair of electrodes.

In another implementation, an electrode device for delivering electrical pulse stimuli to patient's cochlear region includes: a lead comprising two or more elongate insulated electrical conductors; an array of two or more electrodes disposed at a distal end of the lead, individual electrodes of the two or more electrodes in electrical communication with a single respective electrical conductor of the two or more electrical conductors; and an anchor element disposed adjacent to the pair of electrodes.

Such an electrode device may optionally include at least four electrical conductors and the array of two or more electrodes may include at least four electrodes.

In another implementation, a method of treating a tinnitus condition of a patient includes implanting the electrode device as described herein within the patient, wherein said implanting comprises placing electrodes of the electrode device on a cochlear bone, including the promontory, of the patient; and delivering, via the electrodes, electrical pulse stimuli to the cochlear bone (e.g., promontory) of the patient.

In another implementation, a method of intraosseously treating a tinnitus condition of a patient includes: drilling a hole (e.g., a blind hole) in a cochlear bone of the patient, wherein said drilling comprises creating a hole in the cochlear bone without penetrating through the cochlear bone into the cochlear lumen; implanting an electrode device within the patient, wherein said implanting comprises intraosseously placing one or more electrodes of the electrode device within the hole; and delivering, via the one or more electrodes, electrical pulse stimuli to the cochlear bone of the patient.

In another implementation an electrode device for delivering electrical pulse stimuli shallowly within a patient's cochlea includes: a lead comprising a one or more elongate insulated electrical conductors; one or more electrodes disposed at a distal end of the lead, individual electrodes of the one or more electrodes in electrical communication with respective ones of the one or more electrical conductors; and an anchor element disposed adjacent to the one or more electrodes, wherein the anchor element is a flexible barbed member.

In another implementation, a method of treating a tinnitus condition of a patient includes: implanting the electrode device for delivering electrical pulse stimuli shallowly within a patient's cochlea within the patient. The implanting includes placing the one or more electrodes and the flexible barbed member within a cochlea of the patient while portions of the lead proximal to the flexible barbed member are not within the cochlea; and delivering, via the one or more electrodes, electrical pulse stimuli shallowly within the cochlea of the patient.

In another implementation, an electrode device for delivering electrical pulse stimuli to a patient's vestibulocochlear nerve includes: a lead comprising a one or more elongate insulated electrical conductors; and one or more electrodes disposed on a distal end portion of the lead, individual electrodes of the one or more electrodes in electrical communication with respective ones of the one or more electrical conductors, wherein the distal end portion comprises a malleable member that retains a shape after being bent into the shape.

In another implementation, a method of treating a tinnitus condition of a patient includes: implanting the electrode device for delivering electrical pulse stimuli to a patient's vestibulocochlear nerve within the patient. The implanting includes wrapping the distal end portion around the patient's vestibulocochlear nerve; and delivering, via the one or more electrodes, electrical pulse stimuli to the patient's vestibulocochlear nerve.

In another implementation, an electrode device for delivering electrical pulse stimuli to a patient's vestibulocochlear nerve includes: a lead comprising a one or more elongate insulated electrical conductors; and one or more electrodes disposed on a distal end portion of the lead. Individual electrodes of the one or more electrodes in electrical communication with respective ones of the one or more electrical conductors. The distal end portion comprises a shape-memory member that seeks a curved shape when heated.

In another implementation, a method of treating a tinnitus condition of a patient includes: implanting the electrode device for delivering electrical pulse stimuli to a patient's vestibulocochlear nerve within the patient. The implanting includes heating the distal end portion and thereafter positioning the distal end portion around the patient's vestibulocochlear nerve; and delivering, via the one or more electrodes, electrical pulse stimuli to the patient's vestibulocochlear nerve.

In another implementation, a method of treating a tinnitus condition of a patient includes: implanting an electrode device within the patient, wherein the electrode device comprises a lead and a needle electrode having one or more electrodes disposed at a distal end of the lead, wherein said implanting comprises inserting at least a portion of the needle electrode within a vestibulocochlear nerve of the patient; and delivering, via the one or more electrodes, electrical pulse stimuli to the vestibulocochlear nerve of the patient.

Such a method of treating a tinnitus condition of a patient may optionally include one or more of the following features. The electrode device may include an anchor element pivotably coupled to the needle electrode. The needle electrode may be at least partially malleable. The method may also include bending a malleable portion of the needle electrode around the vestibulocochlear nerve of the patient.

In another implementation, a method of treating a balance-deficiency condition of a patient includes: implanting an electrode device within the patient in the region of semicircular canals and vestibule at a surface, intraosseous and/or subendosteal, or intra-labyrinthine position; and delivering, via the one or more electrodes, electrical pulse stimuli to stimulate labyrinthine function of the patient.

Particular embodiments of the subject matter described in this document can be implemented to realize one or more of the following advantages. Cochlear surface electrode(s), intraosseous electrode(s), endosteal electrode(s), subendosteal electrode(s) or short intracochlear electrode(s) (or a combination thereof), connected to a receiver/stimulator electronics package, can provide an effectual long-term treatment of tinnitus in many patients. Some embodiments described herein include a grid array, linear array, paired array or single stimulation electrode(s). A multi-electrode array can advantageously provide broad spatial coverage of the cochlear region. Additionally, various electrode pairs or groupings within the multi-electrode array can be activated (while others are deactivated) to provide a customized stimulation treatment that is effective for a particular patient's needs. In some embodiments, one or more electrodes can be placed intraosseously (e.g., in the cochlear bone). Such intraosseous placement can provide the advantage of delivering electrical stimulation in closer proximity to the cochlea (as compared to promontory surface placement). Other devices provided herein can advantageously deliver electrical stimulation to the vestibulocochlear nerve to treat tinnitus.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DETAILED DESCRIPTION

This document provides devices for treating tinnitus and methods of using the devices to treat tinnitus. For example, this document provides implantable electrodes and stimulation devices for delivering electrical stimulation to the cochlear region to treat tinnitus. Cochlear surface electrode(s), endosteal electrode(s), subendosteal electrode(s), intraosseous electrode(s), or short intracochlear electrode(s) (or a combination thereof), connected to existing but modified cochlear implant receiver/stimulator technology, can provide a successful model for long-term treatment of tinnitus in a large number of patients. In some cases, patients can simply turn on the tinnitus implant when experiencing troublesome tinnitus and gain instant relief. With increasing use, it is likely many patients will enjoy lasting tinnitus suppression, hours and even days after the device is turned off (i.e., residual inhibition).

Using surface, endosteal, subendosteal, intraosseous, or short intracochlear electrodes (or a combination thereof), customized monopolar or bipolar stimulation can be performed to target specific patterns and frequencies of tinnitus. A surface grid of electrodes has the advantage of improved cochlear coverage. Endosteal and/or intraosseous electrodes in the promontory can place the electrical stimulation in closer proximity to the modiolus (the conical central axis of the cochlea) without risking sensorineural hearing loss. A short intracochlear electrode offers a direct method of cochlear stimulation. Devices and methods for each of the aforementioned treatment modalities are described further herein.

Figure 1:
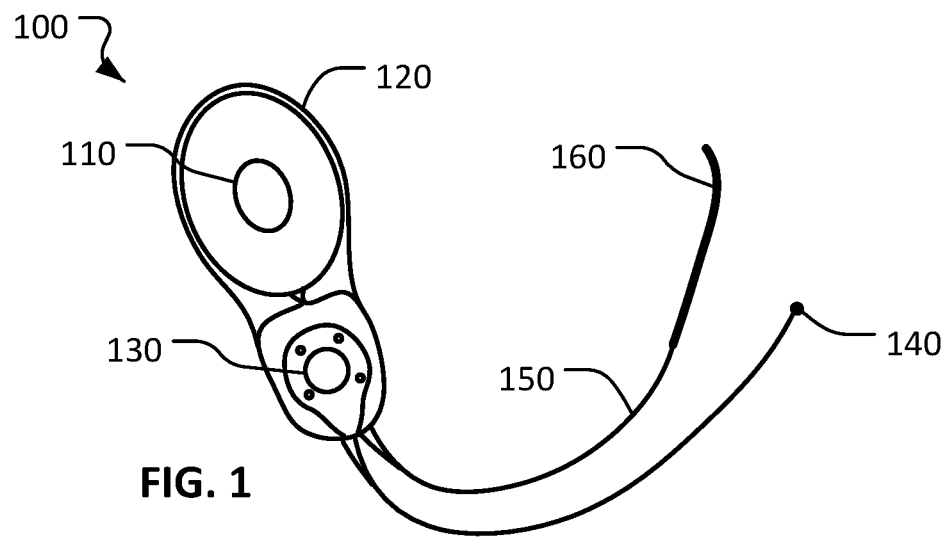
FIG. 1 is an illustration of an example implantable receiver/stimulator device in accordance with some embodiments.

Referring to FIG. 1, an implantable receiver/stimulator device 100 can be used in conjunction with the various types of electrode devices provided herein. Receiver/stimulator device 100 can be functionally akin to an implantable receiver/stimulator device used for cochlear implant electrical stimulation. Accordingly, receiver/stimulator device 100 is implanted under the post-auricular scalp and the lead wire(s) can travel through the mastoid and facial recess to the target electrode location(s). In some cases, for treating tinnitus, the target electrode location may be the bony cochlea, otic capsule, and/or promontory (e.g., endosteally and/or intraosseously). In some cases, for treating balance disorders, the target electrode location may be the bony labyrinth (e.g., surface, intraosseous, or intra-labyrinthine) including the semicircular canals and vestibule. For example, surface, intraosseous, and intra-labyrinthine electrodes can be placed in the region of the semicircular canals and vestibule to stimulate labyrinthine function. Electrical stimulation of this organ may be used to rehabilitate vestibular hypofunction or treat ongoing or recurrent vestibular diseases, such as Meniere's disease.

An external device (not shown) can be used to wirelessly communicate (through the patient's scalp) with the implanted receiver/stimulator device 100. Such an external device can function to activate, program, power, control, and/or otherwise interact with receiver/stimulator device 100. In some cases, receiver/stimulator device 100 can be programmed according to pulse width, current amplitude, stimulus rate, stimulation mode, and the like.

In the depicted embodiment, receiver/stimulator device 100 includes a magnet 110, a receiver coil 120, a stimulator 130, a ground lead 140, a lead wire 150, and one or more electrodes 160. Magnet 110 can be used to magnetically couple and align receiver/stimulator device 100 with an external device. Receiver coil 120 is used to wirelessly communicate with an external device. Stimulator 130 controls the operations of receiver/stimulator device 100 and is the source of electrical stimuli. Lead wire 150 conducts the electrical stimuli to electrode 160.

Electrode 160 delivers the electrical stimuli to tissue of the patient. It should be understood that electrode 160 is representative of any of the embodiments of electrodes described herein. That is, any electrode embodiment described herein can be used for electrode 160. Ground lead 140 provides a path for the electrical stimuli to flow after the stimuli has been passed from electrode 160 to the tissue. It should be understood that the depicted embodiment of receiver/stimulator device 100 provides just one non-limiting example of the types of implantable receiver/stimulator devices that can be used in conjunction with the various types of electrode devices provided herein.

In some cases, prior to permanent electrode 160 placement, test electrodes can be placed on the patient's cochlea region via a transcanal tympanotomy using local anesthetic with the patient awake. An instrument set can be used to apply varying patterns of electrical stimulation, and the patient can convey which pattern resulted in greatest tinnitus reduction. Individual instruments will vary based on the number of electrodes and the distance between electrodes. Additionally, "pitch-masking" (also referred to as frequency matching) and CT imaging may assist in determining optimal electrode 160 positioning.

Figure 2:
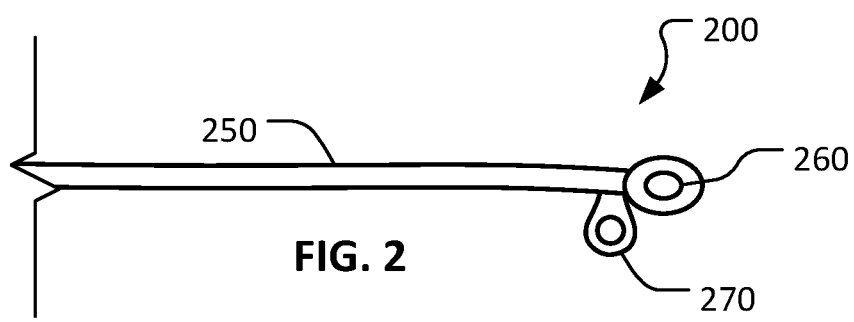
FIG. 2 depicts an example electrode device in accordance with some embodiments provided herein.

Referring to FIG. 2, an example cochlear surface electrode device 200 can be used to deliver electrical pulses in a patient's cochlear region to treat tinnitus. Electrode device 200 includes a lead 250, an electrode 260, and an anchor element 270. Lead 250 is an insulated conductor that puts electrode 260 in electrical communication with a source of electrical pulse stimuli (e.g., receiver/stimulator device 100). Electrode 260 is an uninsulated conductive element that, when placed in contact with tissue, can deliver electrical stimuli to the tissue. Surface electrode device 200 is an example of a monopolar electrode device that can be used to treat tinnitus. Anchor element 270 is attached to lead 250 and/or electrode 260.

In some cases, cochlear surface electrode device 200 is implanted such that electrode 260 is in contact with the patient's cochlear bone (e.g., promontory). Anchor element 270 can be used to couple electrode device 200 to the patient's tissue at the target site, and to provide migration resistance. In some cases, an adhesive (e.g., bone cement and the like) can be used to tack anchor element 270 to tissue (e.g., bone, cartilage, or soft tissue). In some cases, a mechanical anchor such as a screw or barbed member can be used to couple anchor element 270 to tissue. In the depicted embodiment, anchor element 270 defines a fenestration that can receive adhesive and/or a mechanical anchor.

Figure 3:
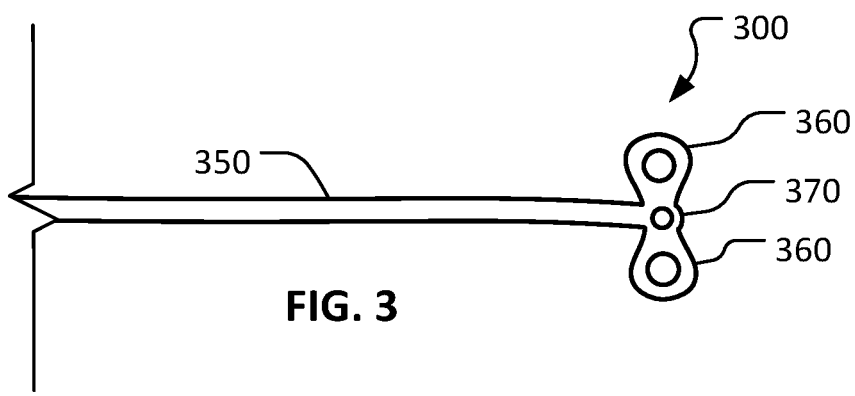
FIG. 3 depicts another example electrode device in accordance with some embodiments provided herein.

Referring to FIG. 3, another example cochlear surface electrode device 300 can be used to deliver electrical pulses in a patient's cochlear region to treat tinnitus. Electrode device 300 includes a lead 350, an electrode pair 360, and an anchor element 370. In some embodiments, surface electrode device 300 is an example of a bipolar electrode device that can be used to treat tinnitus. That is, electrode pair 360 includes two electrodes. In some cases, one of the two electrodes functions as a cathode and the other functions as an anode. Hence, in some cases electrode pair 360, when placed in contact with tissue, can deliver electrical stimuli to the tissue without the need for a separate ground lead (e.g., ground lead 140 as described above in reference to FIG. 1).

In some cases, both electrodes of electrode pair 360 are used as a cathode and a separate ground lead is used.

Similar to anchor element 270 described above, in some embodiments anchor element 370 defines a fenestration or other type of attachment feature that can receive adhesive and/or a mechanical anchor.

Figure 4:
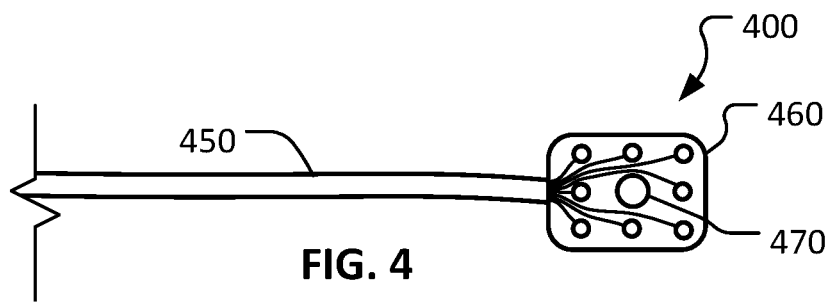
FIG. 4 depicts another example electrode device in accordance with some embodiments provided herein.

Referring to FIG. 4, another example cochlear surface electrode device 400 can be used to deliver electrical pulses in a patient's cochlear region to treat tinnitus. Electrode device 400 includes a lead 450, an electrode array 460, and an anchor element 470. Electrode array 460 can include any number of electrodes arranged in any configuration. Electrode array 460 can comprise a compliant material that can conform to the topography of the patient's tissue (including bone tissue such as the promontory). In some cases, a heat source (e.g., warm water) can be applied to electrode array 460 at the time of placement to increase the compliance of electrode array 460.

Surface electrode device 400 is an example of a grid electrode device that can be used to treat tinnitus. That is, grid electrode array 460 includes two or more electrode pairs. In some cases, one electrode of each of the electrode pair(s) functions as a cathode and the other functions as an anode.

In some cases, individual electrode pairs of the two or more electrode pairs of electrode array 460 can be activated individually. That is, while some electrode pairs are utilized to deliver electrical stimuli, other electrode pairs can be selectively deactivated. In that manner, particular areas or zones of the patient's target tissue (e.g., cochlear region) can receive pulse stimuli, while other areas or zones do not. This functionality can be used to customize the treatment to best suit a particular patient. For example, various electrode pairs (or combinations of electrode pairs) can be experimentally activated to determine which electrode pairs provide the patient with the most relief from tinnitus symptoms.

Figure 5:
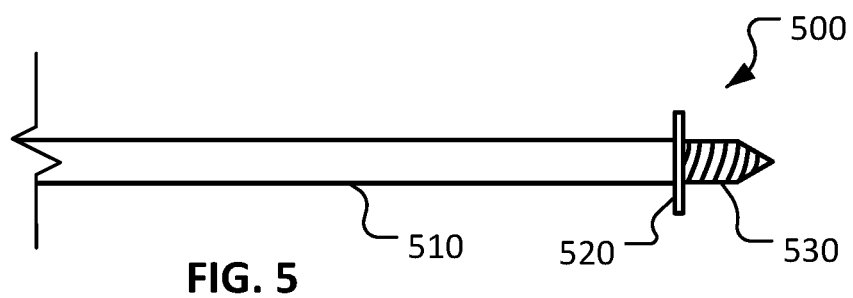
FIG. 5 depicts an example drilling tool in accordance with some embodiments provided herein.
Figure 6:
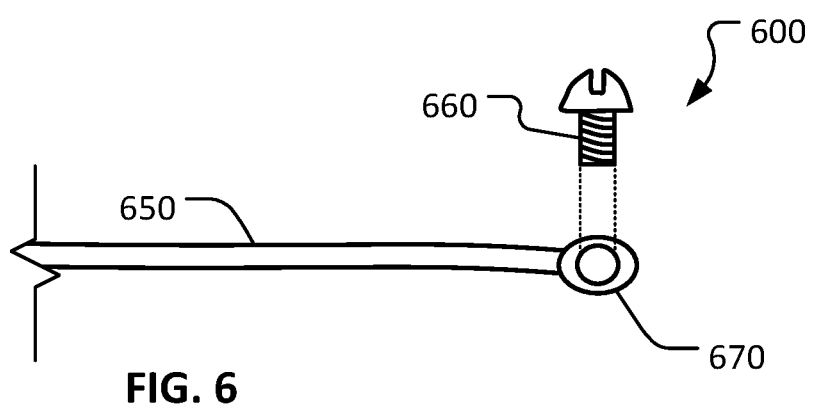
FIG. 6 depicts another example electrode device in accordance with some embodiments provided herein.
Figure 7:
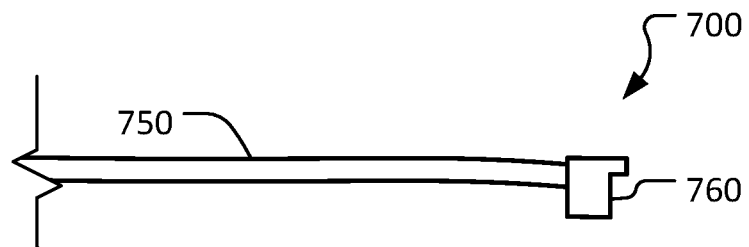
FIG. 7 depicts another example electrode device in accordance with some embodiments provided herein.

Referring to FIGS. 5-7, in accordance with some embodiments provided herein, in some cases one or more electrodes can be placed endosteally and/or intraosseously to treat tinnitus. For example, in some cases one or more electrodes of the present disclosure can be placed intraosseously in the bone tissue of the otic capsule (e.g., without penetrating through the endostium of the cochlea or cochlear lumen). Endosteal and/or intraosseous electrodes can place the electrical stimulation in close proximity to the modiolus (the conical central axis of the cochlea) without risking sensorineural hearing loss. The devices depicted in FIGS. 5-7 can be used for such an implementation.

FIG. 5 depicts a drill device 500 that can be used with a rotary driver instrument. Drill device 500 includes a shank 510, a depth limiter 520, and a working portion 530. Working portion 530 includes cutting edges that can remove tissue such as bone tissue to create a hole (e.g., such as a blind hole or through hole) in the target tissue layer (e.g., anywhere on the promontory including near or at the oval window, near or at the round window, etc.). The maximum depth of the hole can be controlled by depth limiter 520 (e.g., a flange portion). Depth limiter 520 can advantageously prevent the hole created from being a through-hole (i.e., from penetrating completely through the opposite side of the tissue layer, or into the cochlear lumen).

Patient populations naturally have differing anatomical features (such as promontory thicknesses and the like). Accordingly, a variety of differently sized drill devices 500 can be available so as to suit an individual patient's anatomy. For example, a set of drill devices 500 with depth limiter 520 at differing positions can be provided so that a particular drill device 500 can be used for a particular patient to make a hole of the proper depth for the particular patient's anatomy.

In most cases, the most suitable drill device 500 and/or electrode device for a particular patient can be determined in advance of the implant procedure. For example, in some cases a patient can undergo a pre-operative imaging procedure, such as a computerized tomography (CT) scan, to determine the patient's anatomical features such as, but not limited to, promontory thickness. Based on the inventor's investigations, minimal promontory thickness is about 0.4-0.5 mm and maximal promontory thickness is about 2.0-2.2 mm. Thus, a desirable hole depth (and intraosseous electrode length) can be about 0.3 mm to about 0.7 mm, or about 0.5 mm to about 0.9 mm, or about 0.7 mm to about 1.1 mm, or about 0.9 mm to about 1.3 mm, or about 1.1 mm to about 1.5 mm, or about 1.3 mm to about 1.7 mm, or about 1.5 mm to about 1.9 mm, or about 1.7 mm to about 2.1 mm, and/or anywhere within such ranges. In some cases, a set of multiple drill devices 500 will be made available in 0.2 mm depth increments, or 0.1 mm depth increments.

Referring to FIG. 6, when a hole (e.g., a blind hole that does not completely break through the bone) has been created using drill device 500, electrode device 600 can be attached to the target tissue using the hole. Electrode device 600 includes a lead 650, an electrode screw 660, and an anchor element 670. To install electrode device 600, electrode screw 660 is passed through a fenestration in anchor element 670 and into the hole created using drill device 500.

Electrode screw 660 can serve multiple purposes. First, electrode screw 660 can anchor electrode device 600 endosteally and/or intraosseously to the target tissue (e.g., bony cochlea or labyrinth). Secondly, electrode screw 660 can include an electrode core that can deliver electrical pulse stimuli to the tissue with which it makes contact. A set of electrode screws 660 having differing lengths can be available so that a particular electrode screw 660 having a suitable length can be selected for a particular patient. Hence, in some cases, electrode device 600 can deliver electrical stimuli endosteally and/or intraosseously (e.g., to the promontory) to treat tinnitus. In some cases, an adhesive such as bone cement can be used in conjunction with electrode screw 660.

Referring to FIG. 7, when a hole has been created using drill device 500, electrode device 700 can be attached to the target tissue within the hole. Electrode device 700 includes a lead 750 and an electrode lug 760. To install electrode device 700, electrode lug 760 is placed into the hole created using drill device 500. In some cases, an adhesive (e.g., bone cement) can be used to fixate electrode lug 760 in the blind hole. Electrode lug 760 can include an electrode core that can deliver electrical pulse stimuli to the tissue with which it makes contact. A set of electrode devices 700 having differing lengths of electrode lugs 760 can be available so that a particular electrode device 700 having a suitable length of electrode lug 760 can be selected for a particular patient. Hence, in some cases, electrode device 700 can deliver electrical stimuli endosteally and/or intraosseously to a cochlear bone (e.g., to the promontory) to treat tinnitus.

Figure 8:
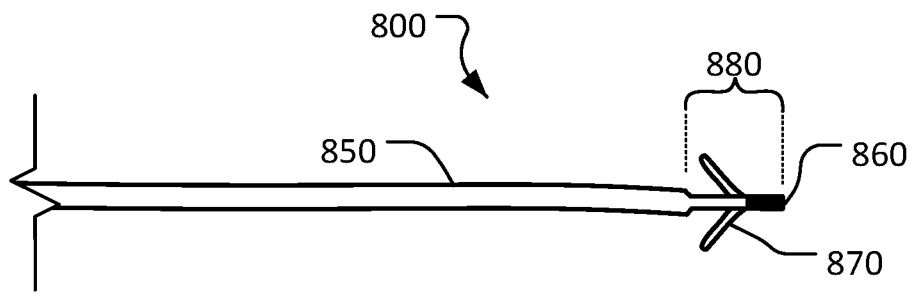
FIG. 8 depicts another example electrode device in accordance with some embodiments provided herein.

Referring to FIG. 8, another example electrode device 800 can be used to deliver electrical pulses in a patient's cochlear region to treat tinnitus. Electrode device 800 includes a lead 850, one or more electrodes 860, and an anchor element 870.

Electrode device 800 is configured for delivering electrical stimuli shallowly within the patient's cochlea lumen. That is, in some cases a distal end portion 880 of electrode device 800 can be inserted within the patient's cochlea (e.g., through the round window or oval window). In such a case, anchor element 870 can act as a soft, flexible barb member to retain distal end portion 880 shallowly within the patient's cochlea. In that arrangement, electrode(s) 860 can thereafter deliver electrical pulses to the patient's cochlea to treat tinnitus.

Figure 9:
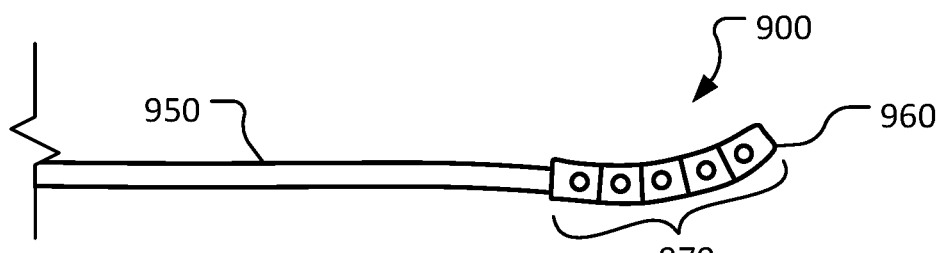
FIG. 9 depicts another example electrode device in accordance with some embodiments provided herein.
Figure 10:
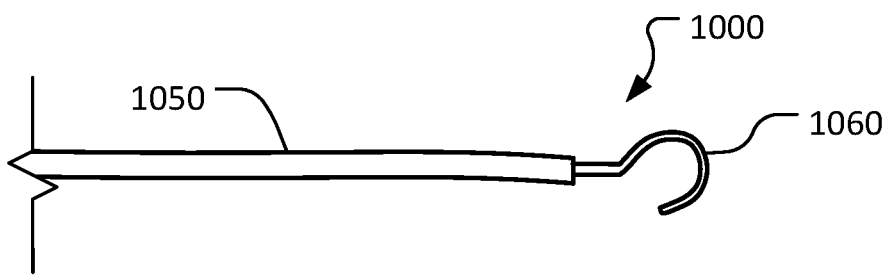
FIG. 10 depicts another example electrode device in accordance with some embodiments provided herein.

Referring to FIGS. 9 and 10, in accordance with some embodiments provided herein, in some cases devices having one or more electrodes can deliver electrical stimulation to the vestibulocochlear nerve to treat tinnitus. The devices depicted in FIGS. 9 and 10 can be used for such an implementation.

Referring to FIG. 9, another example electrode device 900 can be used to deliver electrical pulses in a patient's vestibulocochlear nerve region (e.g., vestibulocochlear nerve or cochlear nerve or vestibular nerve) to treat tinnitus. Electrode device 900 includes a lead 950 and an electrode array 960 disposed on a flexible band 970. Electrode array 960 can include any number of electrodes arranged in any configuration. Electrode array 960 can be monopolar or bipolar.

Flexible band 970 can comprise a compliant material that can be wrapped around the patient's vestibulocochlear nerve. In some cases, a heat source (e.g., warm water) can be applied to flexible band 970 at the time of placement to increase the compliance of flexible band 970. In some cases, flexible band 970 is malleable so that it retains its shape after being wrapped around the patient's vestibulocochlear nerve. Thereafter, electrical pulse stimuli can be delivered to the patient's vestibulocochlear nerve via electrode array 960.

Referring to FIG. 10, another example electrode device 1000 can be used to deliver electrical pulses in a patient's vestibulocochlear nerve region to treat tinnitus. Electrode device 1000 includes a lead 1050 and an electrode hook 1060. Electrode hook 1060 can include one or more than one electrodes arranged in any configuration. Electrode hook 1060 can be monopolar or bipolar.

In some cases, electrode hook 1060 can comprise a shape-memory material that tends to seek a curved or spiral shape such that electrode hook 1060 will be wrapped around the patient's vestibulocochlear nerve. In some cases, a heat source (e.g., electrical current, a laser, and the like) can be applied to electrode hook 1060 at the time of placement to activate the shape-memory property of electrode hook 1060. Thereafter, electrode hook 1060 will tent to retain its shape after being wrapped around the patient's vestibulocochlear nerve. Electrical pulse stimuli can then be delivered to the patient's vestibulocochlear nerve via electrode hook 1060.

Figure 11:
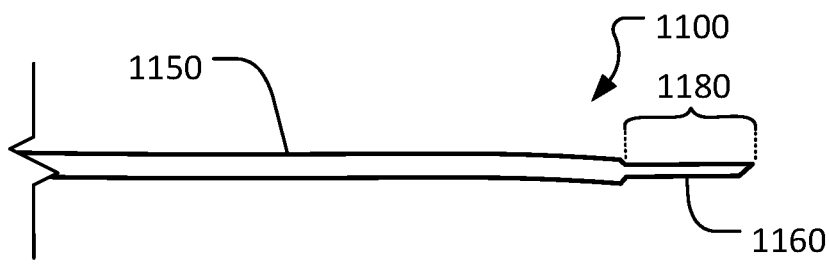
FIG. 11 depicts another example electrode device in accordance with some embodiments provided herein.
Figure 12:
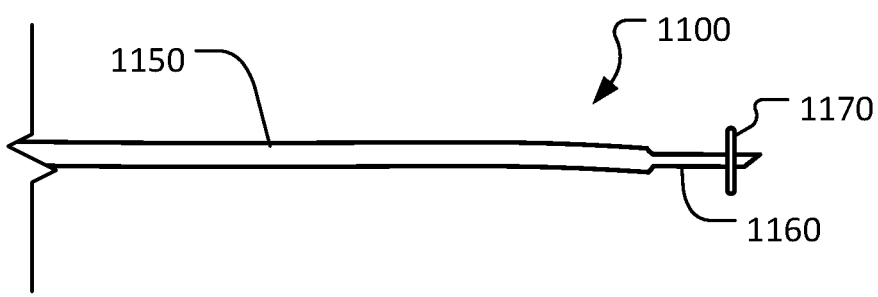
FIG. 12 depicts the electrode device of FIG. 11 in a second configuration.
Figure 13:
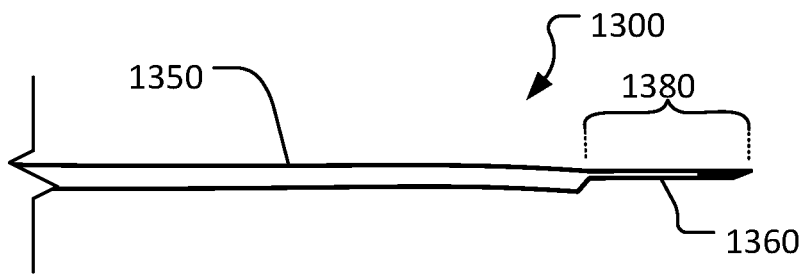
FIG. 13 depicts another example electrode device in accordance with some embodiments provided herein.

Referring to FIGS. 11-13, in accordance with some embodiments provided herein, in some cases devices having one or more electrodes can deliver electrical stimulation within the vestibulocochlear nerve to treat tinnitus. The devices depicted in FIGS. 11-13 can be used for such an implementation. That is, distal end portions of the electrode devices can penetrate and remain within the patient's vestibulocochlear nerve to treat tinnitus.

Referring to FIGS. 11 and 12, another example electrode device 1100 can be used to deliver electrical pulses in a patient's vestibulocochlear nerve region to treat tinnitus. Electrode device 1100 includes a lead 1150, an electrode needle 1160, and an anchor element 1170. Electrode needle 1160 can include one or more than one electrodes arranged in any configuration. Electrode needle 1160 can be monopolar or bipolar.

Electrode device 1100 includes a distal end portion 1180. Distal end portion 1180 can be inserted within the patient's vestibulocochlear nerve while electrode device 1100 is configured as shown in FIG. 11. Thereafter, anchor element 1170 can be pivoted to the configuration shown in FIG. 12. In that configuration, anchor element 1170 acts as an anchor to provide migration resistance. Electrical pulse stimuli can then be delivered to within the patient's vestibulocochlear nerve via electrode needle 1160.

Referring to FIG. 13, another example electrode device 1300 can be used to deliver electrical pulses in a patient's vestibulocochlear nerve region to treat tinnitus. Electrode device 1300 includes a lead 1350 and an electrode needle 1360. Electrode needle 1360 can include one or more than one electrodes arranged in any configuration. Electrode needle 1360 can be monopolar or bipolar.

Electrode device 1300 includes a distal end portion 1380. In some cases, distal end portion 1380 is malleable. Distal end portion 1380 can be inserted within and/or through the patient's vestibulocochlear nerve. Thereafter, a portion of distal end portion 1380 can be bent to wrap distal end portion 1380 around the patient's vestibulocochlear nerve. In that configuration, distal end portion 1380 acts as an anchor to provide migration resistance. Electrical pulse stimuli can then be delivered to within and/or on the patient's vestibulocochlear nerve via electrode needle 1360.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of intraosseously treating a tinnitus condition of a patient, the method comprising:
   providing:
      a stimulator device having exactly two leads extending therefrom, a first lead of the two leads being a ground lead and a second lead of the two leads being a stimulation lead, the ground lead and the stimulation lead being separated leads that individually extend separately from the stimulator device;

a ground electrode at an end of the ground lead; and a single solid electrode at an end of the stimulation lead;

performing a pre-operative imaging procedure to measure a thickness of a cochlear bone of the patient;

using the measured thickness of the cochlear bone to select a cochlear bone drilling depth that is less than the measured thickness of the cochlear bone;

drilling a hole in the cochlear bone of the patient to the selected cochlear bone drilling depth so that the drilling creates a blind hole in the cochlear bone without completely breaking through the cochlear bone;

intraosseously placing the single solid electrode within the blind hole; and delivering, via the single solid electrode, a pattern of electrical pulse stimuli to the cochlear bone of the patient to reduce the tinnitus condition.

2. The method of claim 1, wherein the drilling comprises using a drill device with cutting edges that remove bone tissue to create the hole.

3. The method of claim 2, wherein the drilling comprises using a rotary driver instrument with the drill device.

4. The method of claim 2, wherein the drill device comprises a depth limiter.

5. The method of claim 4, wherein the depth limiter controls a maximum depth of the blind hole.

6. The method of claim 1, wherein the drilling creates the blind hole in the patient's promontory.

7. The method of claim 6, wherein the blind hole has a depth of 1.1 mm to 1.5 mm.

8. The method of claim 6, wherein the blind hole has a depth of 0.9 mm to 1.3 mm.

9. The method of claim 6, wherein the blind hole has a depth of 1.3 mm to 1.7 mm.

10. The method of claim 1, further comprising, after intraosseously placing the single solid electrode within the blind hole, using an adhesive to fixate the single solid electrode within the blind hole.

11. The method of claim 10, wherein the adhesive is bone cement.

12. The method of claim 1, further comprising placing the stimulator device under a post-auricular scalp of the patient, and wherein the pattern of electrical pulse stimuli is sourced from the stimulator device.

13. The method of claim 12, wherein the pattern of electrical pulse stimuli sourced from the stimulator device is controllable according to pulse width, amplitude, and stimulus rate.

14. The method of claim 1, wherein the pre-operative imaging procedure is a computerized tomography scan procedure.

15. The method of claim 1, further comprising selecting a drill device with a depth limiter that equals the selected cochlear bone drilling depth.

* * * * *